United States Patent
Curran et al.

(10) Patent No.: US 6,372,906 B1
(45) Date of Patent: Apr. 16, 2002

(54) SYNTHESIS OF SILYL CAMPTOTHECINS AND SILYL HOMOCAMPTOTHECINS

(75) Inventors: Dennis P. Curran; Wu Du, both of Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/833,757

(22) Filed: Apr. 12, 2001

(51) Int. Cl.$^7$ .................... C07D 491/22; C07D 491/147

(52) U.S. Cl. .................................... 546/14; 546/48
(58) Field of Search ...................... 546/14, 48

(56) References Cited

U.S. PATENT DOCUMENTS

| | | |
|---|---|---|
| 5,468,859 A | 11/1995 | Fortunak |
| 5,700,939 A | 12/1997 | Fortunak |
| 5,744,605 A | 4/1998 | Curran |
| 6,057,303 A | 10/1998 | Haridas |
| 5,910,491 A | 6/1999 | Hausheer |
| 5,935,967 A | 8/1999 | Hausheer |
| 6,150,343 A | 11/2000 | Curran |
| 6,207,832 B1 | 3/2001 | Curran |
| 6,211,371 B1 | 4/2001 | Curran |
| 6,252,079 B1 | 6/2001 | Curran |

FOREIGN PATENT DOCUMENTS

| | | |
|---|---|---|
| WO | WO/97/00876 | 1/1997 |
| WO | WO98/07727 | 2/1998 |
| WO | WO98/28305 | 7/1998 |
| WO | WO98/35940 | 8/1998 |
| WO | WO99/11646 | 3/1999 |
| WO | WO 00/50427 | 8/2000 |

OTHER PUBLICATIONS

Curran, D.P. and Liu, H., "New 4+1 Radical Annulations—A Formal Total Synthesis of (+/–)–Camptothecin," J. Am. Chem Soc., 114, 5863–5864 (1992). Published Jul. 1, 1992.

Curran, D.P., "The Camptothecins—A reborn Family of Antitumor Agents", J. Chin. Chem. Soc., 40, 1–6 (1993). Published Feb., 1993.

Curran, D.P. et al., "Recent Applications of Radical Reactions in Natural Product Synthesis," Pure Appl. Chem., 65, 1153–1159 (1993). Published Jun. 1993.

Curran, D.P. et al., "Cascade Radical Reactions of Isonitriles: A Second–Generation Synthesis of (20S)–Camptothecin, Topotecan, Irinotecan, and GI–147211C," Angew. Chem. Int. Ed, 34, 2683–2684 (1995). Published Jan. 5, 1996.

Curran, D.P., Liu, H.; Josien H; Ko, S.B., "Tandem Radical Reactions of Isonitriles with 2–pyrdonyl and other aryl radicals: Scope and Limitations, and a First Generation Sunthesis of (+/–)–Camptothecin," Tetrahedron, 52, 11385–11404 (1996). Published Aug. 1996.

Josien, H. et al., "Synthesis of (S)–mappicine and Mappicine Ketone Via Radical Cascade Reaction of Isonitirles," Tetrahedron, 53, 8881–8886 (1997). Published Jun. 30, 1997.

Josien, H. et al., "7–Silylcamptothecins (Silatecans): A New Family of Camptothecin Antitumor Agents," Bioorg. Med. Chem. Lett. 7, 3189–3295 (1997).

Josien, H. et al., "A General Synthetic Approach to the (20S)–Camptothecin Family of Antitumor Agents by a Regiocontrolled Cascade Radical Cyclization of Aryl Isonitriles," Chem. Eur. J. 4, 67–83 (1998). Published Jan. 1998.

Bom, D. et al., "Novel A,B,E–ring Modified Camptothecins Displaying High Lipophilicity and Markedly Improved Human Blood Stabilities," J. Med. Chem, 42:3018–3022 (1999).

Pollack et al., "Potent Topoisomerase I Inhibition by Novel Silatecans Eliminates Glioma Proliferation In Vitro and In Vivo," Cancer Research, 59, 4898–4505.

Bom, D. et al., "The Novel Silatecan 7–tert–Butlydimethylsilyl–10–hydroxycamptothecin Displays High Lipophilicity, Improved Human Blood Stability, and Potent Anticancer Activity," J. Med. Chem, 43, 3970–3980 (2000).

Minisci, F., et al., "Recent Developments of Free Radical Substitutions of Heteroaromatic Bases," Heterocycles, 28, 489 (1989).

Sawada, S. et al., "Synthesis of CPT–11 (Ironotecan Hydrochloride Trihydrate)" in The Camptothecins: From Discovery to Patient, P. Pantanzis et al., Ed., NY Acad. Sci., New York, NY, vol. 803, 13–28*1996).

Chatgilialoglu, C. et al., "Sulfur–centered Radicals," Chem. Rev, 95, 1229–1251 (1995).

Roberts, B.P., "Polarity–reversal Catalysis of Hydrogen–Atom Abstraction Reactions: Concepts and Applications in Organic Chemistry," Chem. Soc. Rev., 28, 25–35 (1999).

Zavistas, A.A., et al., "Energies of Activation. The paradigm of Hydrogen Abstractions by Radicals", J. Am. Chem. Soc., 117, 10645–10654 (1995).

Curran, D.P. et al., The Cascade Radical Annulation Approach to New Analogs of Camptothecin: Combinatorial Synthesis of Silatecans and Homosilatecans, In The Camptothecins: Unfolding their Anticancer Potential, vol. 922, 112–121 (2000).

Primary Examiner—Charanjit S. Aulakh
(74) Attorney, Agent, or Firm—Bartony & Hare

(57) ABSTRACT

A method of synthesizing 7-silyl camptothecins and 7-silyl homocamptothecins includes the step of mixing a camptothecin or a homocamptothecin having hydrogen at the C7 position with a silyl radical generator and a silyl radical precursor under conditions to generate a silyl radical. $SiR^1R^2R^3$ wherein $R^1$, $R^2$ and $R^3$ are independently a $C_{1-10}$ alkyl group, a $C_{2-10}$ alkenyl group, a $C_{2-10}$ alkynyl group, an aryl group, $-(CH_2)_m R^{11}$ or $SiR^{12}R^{13}R^{14}$, wherein m is an integer within the range of 1 through 10 and $R^{11}$ is a hydroxy group, an alkoxy group, an amino group, an alkylamino group, a dialkylamino group, F, Cl, a cyano group, $-SR^c$ or a nitro group, and wherein $R^{12}$, $R^{13}$ and $R^{14}$ are independently the same or different an alkyl group or an aryl group.

39 Claims, 5 Drawing Sheets

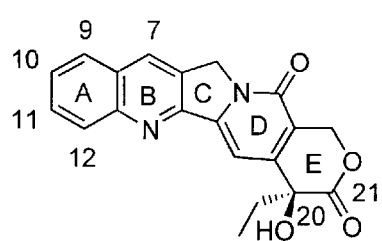
20(S)-camptothecin
1a
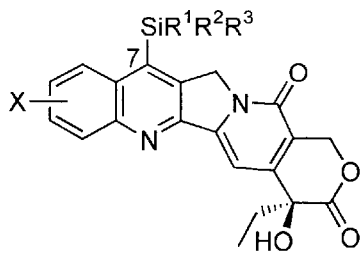
"silatecans"
X = OH, NH$_2$, H, etc.
R$^1$, R$^2$ and R$^3$ = alkyl or aryl
2
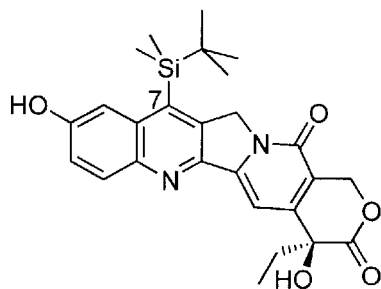
DB-67
2a
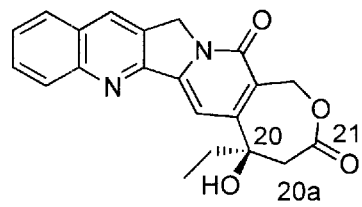
homocamptothecin
10a
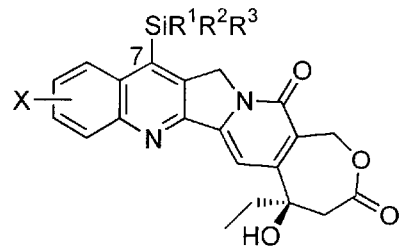
"homosilatecans"
X = OH, NH$_2$, H, etc.
R$^1$, R$^2$ and R$^3$ = alkyl or aryl
11
Figure 1. Camptothecin, Silatecans, Homocamptothecin and homosilatecans

SYNTHESIS OF SILYL CAMPTOTHECINS AND SILYL HOMOCAMPTOTHECINS

GOVERNMENT INTEREST

This invention was made with government support under grant RO1 GM33372 awarded by the National Institutes of Health. The government has certain rights in this invention.

BACKGROUND OF THE INVENTION

The present invention relates to the synthesis of silyl camptothecins and silyl homocamptothecins and, particularly, to synthesis of silyl camptothecins and silyl homocamptothecins via a semisynthetic route from camptothecins and homocamptothecins.

References set forth herein may facilitate understanding of the present invention or the background of the present invention. Inclusion of a reference herein, however, is not intended to and does not constitute an admission that the reference is available as prior art with respect to the present invention.

The structure of camptothecin 1a and homocamptothecin 10a are illustrated in FIG. 1. The core structure of the camptothecin class of molecules has five fused rings, A–E. Standard substituents include hydroxyl and ethyl at C20, and other positions of the camptothecin ring core can also be substituted. Homocamptothecin has the same A–D rings as camptothecin, but the E-ring contains an additional methylene group (C20a). The A–B ring system of the camptothecin and homocamptothecin is a quinoline, and this part of the ring system is especially important since substituents in the quinoline part of the molecule often impart useful properties, as detailed below.

In general, camptothecins and homocamptothecins (sometimes referred to generally herein as camptothecins or the camptothecin family) are DNA topoisomerase I inhibitors useful, for example, as anticancer drugs. Analogs of the natural product camptothecin are among the most important classes of compounds available for treatment of solid tumors. Topotecan (tpt) and CPT-11 were the first two members in the camptothecin family to gain United States Food and Drug Administration full approval status (topotecan in 1996 as second-line therapy for advanced epithelial ovarian cancer, topotecan again in 1998 for the treatment of small cell lung cancer, CPT-11 in 1998 as first-line therapy for colon cancer).

Lavergne et al. have shown that expansion of the E-ring of camptothecin to produce a "homocamptothecin" enhances the solution stability of camptothecin while maintaining anticancer activity. Lavergne, O., Lesueur-Ginot, L., Rodas, F. P., Kasprzyk, P. G., Pommier, J., Demarquay, D., Prevost, G., Ulibarri, G., Rolland, A., Schiano-Liberatore, A.-M., Harnett, J., Pons, D., Camara, J., Bigg, D., "Homocamptothecins: Synthesis and Antitumor Activity of Novel E-Ring Modified Camptothecin Analogs", J. Med. Chem., 41, 5410–5419 (1998); and Lavergne, O., Lesueur-Ginot, L., Rodas, F. P., and Bigg, D., "An E-Ring Modified Camptothecin With Potent Antiproliferative and Topoisomerase I Inhibitory Activities," Bioorg. Med. Chem. Lett. 7, 2235–2238 (1997). The modification to the E-ring in the studies of Lavergne et al. involved insertion of a methylene spacer between the carbon bearing the 20-OH functionality and the carboxyl group of the naturally occurring six-membered α-hydroxylactone of camptothecin. Incorporation of the new 7-membered β-hydroxylactone ring into camptothecin has been found to improve the solution stability of the agent. Despite the structural similarity to camptothecins, homocamptothecins behave very differently under physiological conditions. In general, standard camptothecin analogs are dynamic drugs because their lactone rings open rapidly and reversibly under physiological conditions. Typically, the lactone rings of homocamptothecins open comparatively slowly and irreversibly.

7-Silyl camptothecins 2 and 7-silyl homocamptothecins 11 (sometimes referred to as silatecans and homosilatecans) as illustrated in FIG. 1 are important classes of lipophilic camptothecin analogs, See, for example, a) Josien, H.; Bom, D.; Curran, D. P.; Zheng, Y.-H.; Chou, T.-C. Bioorg Med. Chem. Lett., 7, 3189 (1997); b) Pollack, I. F.; Erff, M.; Bom, D.; Burke, T. G.; Strode, J. T.; Curran, D. P. Cancer Research, 59, 4898 (1999); Bom, D.; Du, W.; Garbarda, A.; Curran, D. P.; Chavan, A. J.; Kruszewski, S.; Zimmer, S. G.; Fraley, K. A.; Bingcang, A. L.; Wallace, V. P.; Tromberg, B. J.; Burke, T. G. Clinical Cancer Research, 5, 560 (1999); Bom, D.; Curran, D. P.; Chavan, A. J.; Kruszewski, S.; Zimmer, S. G.; Fraley, K. A.; Burke, T. G. J. Med. Chem., 42, 3018 (1999). Many of the most interesting silatecans and homosilatecans contain one or more additional substituents (for example, hydroxy or amino) in the A ring, and the combination of these substituents can provide significant improvements over either of the corresponding the monosubstituted analogs. For example, 7-tert-butyldimethylsilyl-10-hydroxy camptothecin 2a (DB-67), is currently in late stages of preclinical development. DB-67 and other silatecans and homosilatecans show a number of attractive features including high activity against a broad spectrum of solid tumors, low binding to blood proteins, resistance to lactone opening, high lipophilicity, and potential oral availability among others.

DB-67 and other silatecans and homosilatecans have been prepared by total synthesis using the cascade radical annulation routes. See, for example, U.S. patent application Ser. Nos. 09/007,872, 09/212,178 and 09/209,019, U.S. Pat. Nos. 6,150,343 and 6,136,978, Curran, D. P.; Ko, S. B.; Josien, H. Angew. Chem., Int. Ed. Eng, 34, 2683 (1995) and Josien, H.; Ko, S. B.; Bom, D.; Curran, D. P. Chem. Eur. J., 4, 67 (1998). Those total synthetic routes are highly flexible and allow the preparation of a diverse array of silatecan and homosilatecan analogs by both traditional and parallel routes. However, the total synthesis of silatecans and homosilatecans via cascade radical annulation can require thirteen or more steps and proceeds in about 2% overall yield.

It is very desirable to develop improved synthetic routes for producing silyl camptothecins and silyl homocamptothecins.

SUMMARY OF THE INVENTION

The present invention provides semisynthetic routes to the synthesis of silyl camptothecins and silyl homocamptothecins from camptothecins and homocamptothecins by addition of silyl radicals thereto.

In one aspect, the present invention provides a method of synthesizing a compound having the formula

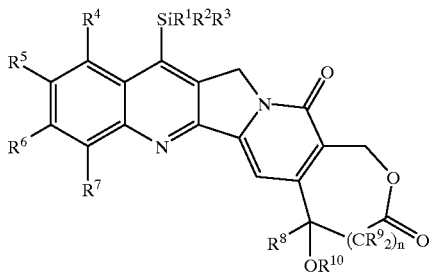

in racemic form, enantiomerically enriched form or enantiomerically pure form, the method including generally the step of reacting a compound having the formula

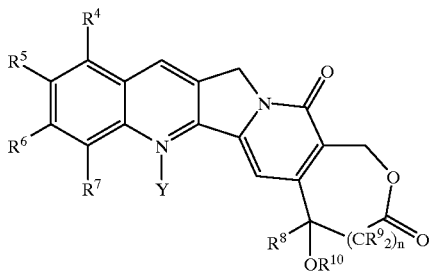

with a silyl radical precursor under conditions to generate a silyl radical. $SiR^1R^2R^3$ wherein $R^1$, $R^2$ and $R^3$ are, for example, independently the same or different a $C^{1-10}$ alkyl group, a $C_{2-10}$ alkenyl group, a $C_{2-10}$ alkynyl group, an aryl group, $-(CH_2)_m R^{11}$, or $SiR^{12}R^{13}R^{14}$, wherein m is an integer within the range of 1 through 10 and $R^{11}$ is a hydroxy group, an alkoxy group, an amino group, an alkylamino group, a dialkylamino group, Cl, F, a cyano group, $-SR^c$ or a nitro group, and wherein $R^{12}$, $R^{13}$ and $R^{14}$ are independently the same or different an alkyl group or an aryl group. Preferably $R^1$, $R^2$ and $R^3$ are independently the same or different an alkyl group or an aryl group.

$R^4$ and $R^5$ are, for example, independently the same or different hydrogen, $-C(O)R^f$ wherein $R^f$ is an alkyl group, an alkoxy group, an amino group or a hydroxy group, an alkyl group, an alkenyl group, an alkynyl group, an alkoxy group, an aryloxy group, an acyloxy group, $-OC(O)OR_d$, wherein $R^d$ is an alkyl group, $-OC(O)NR^aR^b$ wherein $R^a$ and $R^b$ are independently the same or different, H, $-C(O)R^f$, an alkyl group or an aryl group, Cl, F, a hydroxy group, a nitro group, a cyano group, an azido group, a formyl group, a hydrazino group, an amino group, $-SR^c$, wherein $R^c$ is hydrogen, $-C(O)R^f$, an alkyl group or an aryl group; or $R^4$ and $R^5$ together form a chain of three or four members selected from the group of CH, $CH_2$, O, S, NH, or $NR^{15}$, wherein $R^{15}$ is a $C_1$-$C_6$ alkyl group. $R^4$ and $R^5$ together can, for example, form a group of the formula $-O(CH_2)_jO-$ wherein j represents the integer 1 or 2.

$R^6$ is, for example, H, Cl, F, a nitro group, an amino group, a hydroxy group, or a cyano group; or $R^5$ and $R^6$ together form a chain of three or four members selected from the group of CH, $CH_2$, O, S, NH, or $NR^5$. $R^5$ and $R^6$ together can, for example, form a group of the formula $-O(CH_2)_jO-$ wherein j represents the integer 1 or 2.

$R^7$ is, for example, H, F, an amino group, a $C_{1-3}$ alkyl group, a $C_{2-3}$ alkenyl group, a $C_{2-3}$ alkynyl group, a trialkylsilyl group or a $C_{1-3}$ alkoxy group. $R^7$ is preferably H. $R^8$ is, for example, a $C_{1-10}$ alkyl group, an alkenyl group, an alkynyl group, or a benzyl group. $R^8$ is preferably an ethyl group, an allyl group, a benzyl group or a propargyl group. Most preferably, $R^8$ is an ethyl group. $R^9$ is, for example, H, F or $-CH_3$, and n is 0 or 1. $R^{10}$ is, for example, $-C(O)R^f$ or H. Preferably, $R^{10}$ is H or $-C(O)CH_3$.

Y is either absent or is oxygen. In the case that Y is oxygen, the N-oxide is transformed to the corresponding silyl camptothecin or silyl homocamptothecin during the reaction.

Preferred silyl radical precursors for use in the present invention include silanes, disilanes, silylgermanes, silylstannanes, silyl boranes, and acyl silanes. Several preferred silanes, disilanes, silylgermanes, and silylstannanes can be represented by the general formula $XSiR^1R^2R^3$ wherein X is H, $SiR^{17}R^{18}R^{19}$, $GeR^{17}R^{18}R^{19}$ or $SnR^{17}R^{18}R^{19}$, respectively, and wherein $R^{17}$, $R^{18}$, and $R^{19}$ are, for example, independently the same of different an alkyl group or an aryl group. Preferred silyl boranes and acyl silanes can also be represented by the formula $XSiR^1R^2R^3$ wherein $X=-B(OR^d)_2$ and $X=-C(O)R^i$, respectively, wherein $R_i$ is an alkyl group or an aryl group.

In the case of disilanes, silylgermanes, silylstannanes, silyl boranes and acyl silanes, the reaction can be effected by irradiation of the reaction mixture with UV light of a wavelength suitable to cleave the Si—X bond either directly or with sensitization. Additives, as known in the art, for example, sensitizers or (photo-)electron transfer agents, can be present to promote the desired reaction.

In the case of disilanes, the reaction can also be effected chemically by the generation of a reactive radical that will homolytically cleave (by homolytic substitution at silicon) the silicon-silicon bond to generate the silyl radical. Preferred reactive radicals for this method are hydroxy, alkoxy or acyloxyl radicals, and preferred methods of generating these radicals are thermolysis or photolysis of hydrogen peroxide, alkyl hydroperoxides, dialkyl peroxides, alkyl acyl peroxides or diacylperoxides. Other methods of alkoxy radical generation such as thermolysis or photolysis of alkyl hyponitrites are also suitable.

The reaction of silanes ($XSiR^1R^2R^3$, X=H) can also be effected chemically by the generation of a reactive radical that will homolytically cleave (by homolytic substitution of hydrogen) the silicon-hydrogen bond to generate the silyl radical. Preferred reactive radicals for this method are hydroxy, alkoxy or acyloxy, and preferred methods of generating these radicals are thermolysis or photolysis of hydrogen peroxide, alkyl hydroperoxides, dialkyl peroxides, alkyl acyl peroxides or diacylperoxides. Other methods of alkoxy radical generation such as thermolysis or photolysis of alkyl hyponitrites are also suitable.

Other silyl radical precursors and methods of generation of silyl radicals are known to those skilled in the art. See, for example C. Chatgilialoglu, Chem. Rev. 1995, 95, 1229, the disclosure of which is incorporated herein by reference. Substantially any of these precursors or methods can be used in this invention.

In another aspect, the present invention provides generally a method of synthesizng silyl-quinolines for example, at the C4 position of the quinoline structure) by reacting a quinoline with a silyl radical generator and a silyl radical precursor under conditions to generate a silyl radical. $SiR^1R^2R^3$. Quinolines have the

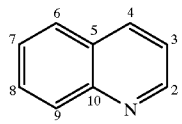

The silyl quinolines of the present invention have the general formula:

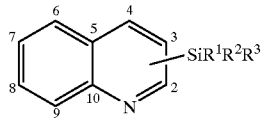

In a preferred embodiment of the silyl radical addition to substituted quinolines, the present invention provides generally a method of synthesizing 7-silyl camptothecins and 7-silyl homocamptothecins including the step of mixing a camptothecins or a homocamptothecin having hydrogen at the C7 position with a silyl radical generator and a silyl radical precursor under conditions to generate a silyl radical •$SiR^1R^2R^3$.

The camptothecin precursors in the reactions of the present invention can be obtained from natural sources, by total synthesis by one of several methods, or by modification of existing synthetic or natural camptothecin analogs. The homocamptothecin precursors for the reactions of the present invention can likewise be obtained by semi-synthesis from camptothecin as, for example, described by Lavergne et al., by total synthesis, or by modification of existing homocamptothecin analogs.

Substituents on the camptothecin and homocamptothecin precursors of the present invention (for example, $R^4$, $R^5$, $R^6$, $R^7$, $R^8$, $R^9$, and $R^{10}$) can be substantially any substituents as known in the art. Substituents on camptothecin and homocamptothecin rings preferably, however, do not react rapidly with silyl radicals of the present invention. In general, reactions of substituents with silyl radicals of the present invention can lead to undesirable byproducts that may be difficult to separate from target products. Examples of suitable substituents include, but are not limited to, $R^4$, $R^5$, $R^6$, $R^7$, $R^8$, $R^9$, and $R^{10}$ set forth above. Examples of substituents that react rapidly with silyl radicals and are preferably avoided include bromine and iodine.

A number of groups, such as amino groups and hydroxy groups, can be protected using protective groups as known in the art before addition of the silyl radical. Preferred protective groups for hydroxy groups include, but are not limited to, acetate and trimethylsilyl groups. Preferred protective groups for amino groups include, but are not limited to, tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis*, Wiley (1991), the disclosure of which is incorporated herein by reference. Such protective groups can be reacted to provide the desired substituent (for example, hydroxy group or an amino group) after addition of the silyl radical using conditions known in the art. In general, protecting groups used in the methods of the present invention are preferably chosen such that they can be selectively removed without affecting the other substituents on the camptothecin ring. In general, 7-silyl substituents on camptothecins (including homocamptothecins) have been found to very stable under a variety of conditions.

Solvents for the reaction can be selected from the full range of traditional organic reaction solvents. Aromatic solvents (for example, benzene and toluene) are less preferred since addition of the silyl radical to the solvent can be a competitive side reaction. Chlorocarbons like chloroform and tetrachloromethane solvents are also less preferred since chlorine abstraction from the solvent by the silyl radical can be a competitive side reaction. However, less reactive chlorocarbons such as 1,2-dichloroethane are more preferred. Other preferred solvents include, ethers (for example tetrahydrofuran (THF), diethylether, dioxane, and the like), alcohols (methanol, ethanol, and the like) and dipolar aprotic solvents ($CH_3CN$, DMF, DMSO, and the like). Water ;need not be excluded from the reaction and can even be used as a cosolvent.

Preferred reaction conditions for generation of silyl radicals from silanes include addition of an organic thiol ($R^{16}SH$, wherein $R^{16}$ is, for example, an alkyl group or a trialkylsilyl group). For example, one set of conditions involved heating a mixture of a camptothecin or homocamptothecin analog, a silane ($R^1R^2R^3SiH$), a peroxide (for example, di-tert-butylperoxide) and a thiol (for example, tert-butane thiol or triisopropylsilane thiol) in an organic solvent. Relative to the camptothecin analog, preferred quantities of the silane range from approximately 1–20 equiv, with approximately 2–10 equiv being more preferred. Preferred quantities of thiol are approximately 0.2–5 equiv, with approximately 1–3 equiv being more preferred. Preferred quantities of the peroxide range from approximately 1–20 equiv with approximately 2–5 equiv being more preferred. Preferred reaction solvents are as discussed above and preferred reaction temperatures range from approximately 60–130° C. Lower reaction temperatures can cause reduced conversion to the product while higher temperatures can cause increased amounts of another product in which the silyl group adds to C12 of the camptothecin precursor (if $R^7$=H). A preferred solvent for these reaction conditions is p-dioxane, and a preferred temperature for reactions in this solvent is at or near the reflux point of p-dioxane. Preferred reaction times are 0.5 to 5 days, with more preferred times being 1–2 days. Preferred thiols include, for example, alkane thiols such as dodecane thiol and tert-butane thiol, and trialkylsilanethiols or triarylsilanethiols such as triisopropylsilanethiol. Trialkylsilanethiols or triarylsilanethiols are generally more preferred.

Thiols are sometimes used in radical chain reaction of silanes to assist in chain propagation of the chain reaction in a process that is often called "polarity reversal catalysis". The silyl additions discovered herein do not appear to be chain reactions, but nonetheless the inventors have discovered that thiols can promote the reaction. The generally mild reaction conditions used with thiols are advantageous in the case of camptothecin and homocamptothecin precursors bearing, for example, acid-sensitive substituents or protective groups.

Silatecans and homosilatecans bearing a 10-hydroxy group have especially interesting biological and chemical properties. The methods of the present invention are well suited for synthesizing such 10-hydroxy silatecans and 10-hydroxy homosilatecans. As the hydroxy group may interfere with the silyl radical generation or addition of prior or subsequent synthetic steps, it may be desirable to use a protecting group as described above or to generate the 10-hydroxy group after addition of the 7-silyl group.

In another aspect, the present invention provides for a compound of the following formula

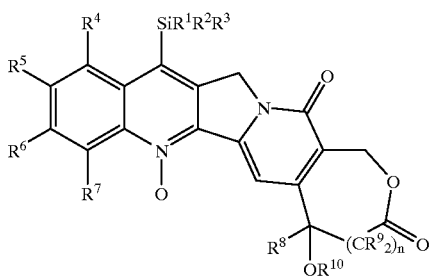

wherein $R^1$—$R^{10}$ are as defined above.

In another aspect, the present invention provides a method for the conversion of a silatecan or homosilatecan lacking any substituent at $R^5$ (that is, $R^5$ is H) to a 10-hydroxysilatecan or 10-hydroxyhomosilatecan analog (that is, $R^5$ is —OH). Converting the hydrogen at $R^5$ to —OH includes generally the step of oxidation to provide an N-oxide, followed by the step of photolysis. The 7-silyl groups of silatecans and homosilatecans have been found to survive the oxidative and acidic reaction conditions used. In a preferred embodiment of this invention, $R^4$, $R^6$ and $R^7$ are also H, and the resulting product is a 10-hydroxysilatecan or homosilatecan.

In this method, the silatecan or homosilatecan is preferably first oxidized to an N-oxide under conditions known to those skilled in the art for this transformation. Preferred conditions are treatment of the silatecan or homosilatecan with hydrogen peroxide in the presence of a carboxylic acid, preferably acetic acid. A mixture of the resulting N-oxide in an organic solvent is then irradiated with light (for example, at the edge of the ultraviolet and visible regions of the spectrum) in the presence of an organic or inorganic acid. Preferred solvents for this reaction are ethers (for example, p-dioxane). The wavelength of irradiated light is preferably in the range of approximately 250–600 nm and more preferably in the range of approximately 275–450 nm. A preferred acid for use in this method is aqueous sulfuric acid in the range of approximately 0.1–5M, preferably approximately 1.0 M, and the preferred amount of the acid relative to the silatecan or homosilatecan is approximately, 1–20 mol equiv, more preferably approximately 1–2 mol equiv.

As indicated above, all compounds of the present invention including the α-hydroxylactone group of silatecans or the β-hydroxylactone group of homosilatecans can exist in racemic form, enantiomerically enriched form, or enantiomerically pure form. The formulas of such compounds as set forth herein cover and/or include each such form.

The terms "alkyl", "aryl" and other groups refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or naphthyl. As used herein, the terms "halogen" or "halo" refer preferably to fluoro and chloro.

The term "alkoxy" refers to —$OR^d$, wherein $R^d$ is an alkyl group. The term "aryloxy" refers to —$OR^e$, wherein $R^e$ is an aryl group. The term acyl refers to —$C(O)R^f$. The term "alkenyl" refers to a straight or branched chain hydrocarbon group with at least one double bond, preferably with 2–15 carbon atoms, and more preferably with 2–10 carbon atoms (for example, —CH=CHR$^g$ or —CH$_2$CH=CHR$^g$). The term "alkynyl" refers to a straight or branched chain hydrocarbon group with at least one triple bond, preferably with 2–15 carbon atoms, and more preferably with 2–10 carbon atoms (for example, —C≡CR$^h$ or —CH$_2$—C≡CR$^h$). The terms "alkylene," "alkenylene" and "alkynylene" refer to bivalent forms of alkyl, alkenyl and alkynyl groups, respectively.

The groups set forth above can be substituted with a wide variety of substituents to synthesize homocamptothecin analogs retaining activity. For example, alkyl groups may preferably be substituted with a group or groups including, but not limited to, a benzyl group, a phenyl group, an alkoxy group, a hydroxy group, an amino group (including, for example, free amino groups, alkylamino, dialkylamino groups and arylamino groups), an alkenyl group, an alkynyl group and an acyloxy group. In the case of amino groups (—$NR^aR^b$), $R^a$ and $R^b$ are preferably independently hydrogen, an acyl group, an alkyl group, or an aryl group. Acyl groups may preferably be substituted with (that is, $R^f$ is) an alkyl group, a haloalkyl group (for example, a perfluoroalkyl group), an aryl group, an alkoxy group, an amino group and a hydroxy group. Alkynyl groups and alkenyl groups may preferably be substituted with (that is, $R^g$ and $R^h$ are preferably) a group or groups including, but not limited to, an alkyl group, an alkoxyalkyl group, an amino alkyl group and a benzyl group.

The term "acyloxy" as used herein refers to the group —$OC(O)R^d$.

The term "alkoxycarbonyloxy" as used herein refers to the group —$OC(O)OR^d$.

The term "carbamoyloxy" as used herein refers to the group —$OC(O)NR^aR^b$.

For purification, administration or other purposes, the E-ring (the lactone ring) may be opened with alkali metal such as, but not limited to, sodium hydroxide or calcium hydroxide, to form opened E-ring analogs of compounds of formula (1) as set forth in the compounds of formula (2). The intermediates thus obtained are more soluble in water and may be purified to produce, after treatment with an acid, a purified form of the camptothecin analogs of the present invention.

BRIEF DESCRIPTION OF THE DRAWINGS

FIG. 1 illustrates the chemical structure of camptothecin, homocamptothecin and several 7-silyl camptothecins and 7-silyl homocamptothecins.

DETAILED DESCRIPTION OF THE INVENTION

Substituents are typically added to the camptothecin ring by the conversion of one existing functional group into another. It is more difficult to introduce new substituents by replacement of existing carbon-hydrogen bonds. Sawada and coworkers used the Minisci reaction to replace hydrogen by alkyl and substituted alkyl groups. See Sawada, S.; Okajima, S.; Aiyama, R.; Nokata, K.; Furuta, T.; Yokokura, T.; Sugino, E.; Yamaguchi, K.; Miyasaka, T. *Chem. Pharm. Bull.*, 39, 1446 (1991); Sawada, S.; Matsuoka, S.; Nokata, K.; Nagata, H.; Furuta, T.; Yokokura, T.; Miyasaka, T. *Chem. Pharm. Bull.*, 39, 3183 (1991); Sawada, S.; Nokata, K.; Furuta, T.; Yokokura, T.; Miyasaki, T. *Chem. Pharm. Bull.*, 39, 2574 (1991); and Minisci, F.; Vismara, E.; Fontana, F. *Heterocycles*, 28, 489 (1989). In that regard, an alkyl aldehyde is typically oxidized with a peroxide and an iron salt in the presence of a camptothecin derivative under strongly acidic conditions to provide a 7-alkyl substituted camptothecin derivative. The reaction is thought to occur through a redox chain mechanism involving the intermediacy of acyl radicals, which decarbonylate to make alkyl radicals. In turn, these alkyl radicals add to camptothecin.

The Sawada/Minisci method for additions of alkyl groups to C7 of camptothecin is not suitable for the addition of silyl radicals, however. The requisite silyl radical precursors, for example $Me_3SiCHO$, are difficult to synthesize and often highly unstable. For example, many such precursors ignite spontaneously on exposure to air. Such compounds have little or no preparative utility and could not survive the vigorous reaction conditions of the Sawada/Minisci approach.

Figure 2:
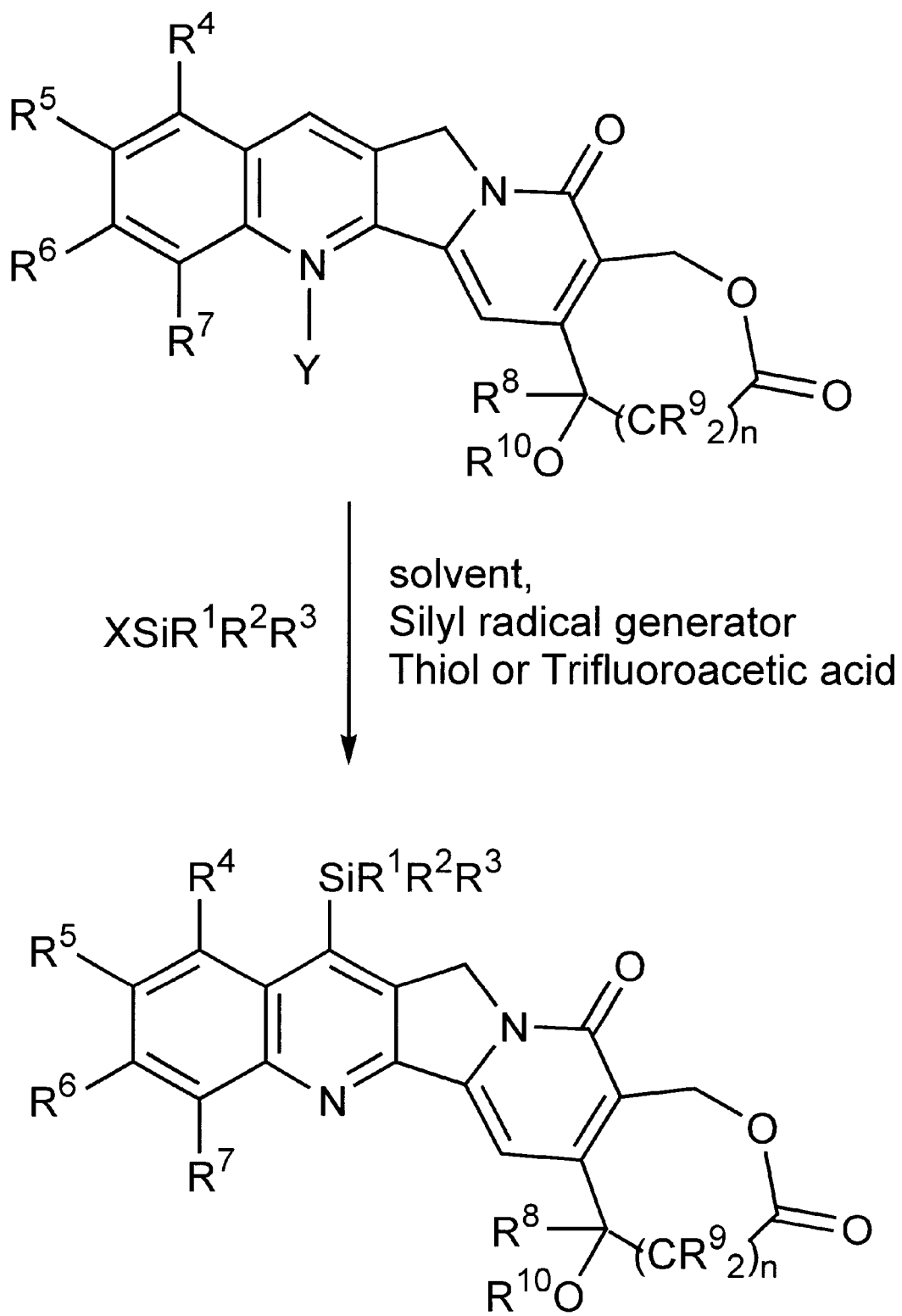
FIG. 2 illustrates a general reaction sequence for synthesis of 7-silyl camptothecins and 7-silyl homocamptothecins.

Nonetheless, the present invention provides a novel semi-synthetic route in which a silyl radical is added at the C7 position of the quinoline ring or B-ring of camptothecins and homocamptothecins and/or at the C12 position of the A-ring of camptothecins and homocamptothecins. In that regard, the present inventors have discovered that the important class of 7-silylcamptothecins and 7-silylhomocamptothecins can be synthesized via reaction of an existing camptothecin or homocamptothecin compounds with known silyl radical precursors having the formula $XSiR^1R^2R^3$ under suitable conditions as described above. A general reaction sequence for synthesis of 7-silyl camptothecin and 7-silyl homocamptothecins is illustrated in FIG. 2. The reaction mixture is worked up by standard methods and the crude reaction product is purified by, for example, chromatography, crystallization, or other standard means to provide the 7-silylcamptothecin (silatecan, n=0) or 7-silylhomocamptothecin (homosilatecan, n=1).

Figure 3:
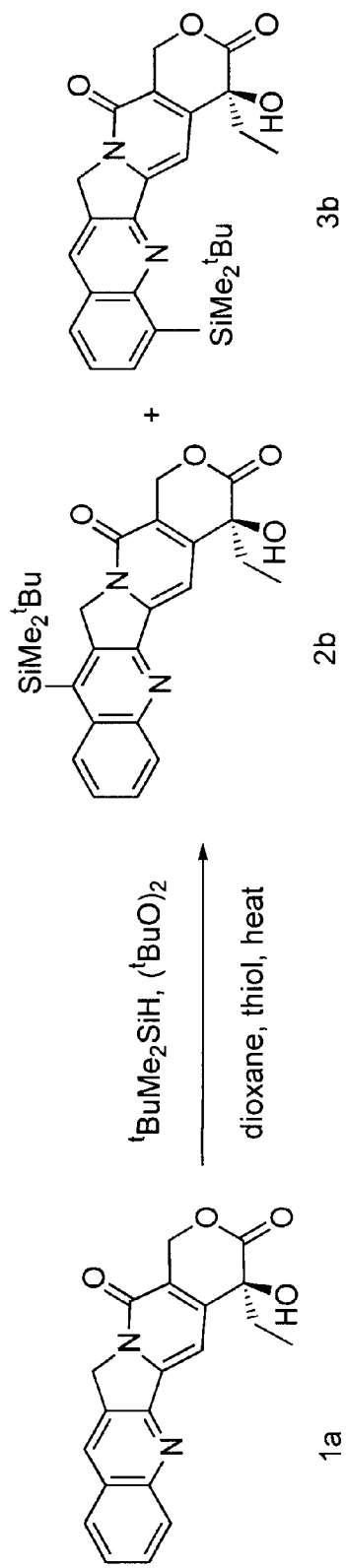
FIG. 3 illustrates reaction of camptothecin with tert-butyldimethyl silane, di-tert-butylperoxide and tert-butane thiol in dioxane to synthesize 7-tert-butyldimethylsilylcamptothecin and 12-tert-butyldimethylsilylcamptothecin.

Several representative studies of the use of silanes ($HSiR^1R^2R^3$) as silyl radical precursors are described herein in discussing the methods of the present invention. In the case that silanes are used as a silyl radical precursor in the methods of the present invention, certain thiols ($R^{16}SH$) were found to have a very beneficial effect as an additive. The results of several experiments are summarized in Table 1 and FIG. 3. For example, heating of camptothecin 1a, tert-butyldimethyl silane (10 equiv), di-tert-butylperoxide (1.7-equiv) and tert-butane thiol (2 equiv) in dioxane at refluxed for 36 h (Table 1, entry 1) followed by chromatographic separation provided (in order of elution) 7-tert-butyldimethylsilylcamptothecin 2b (20%), 12-tert-butyldimethylsilylcamptothecin 3b (10%) and recovered camptothecin 1a (57%). 7-tert-Butyldimethylsilylcamptothecin 2b was identical to an authentic sample prepared by total synthesis. 12-tert-Butyldimethylsilylcamptothecin was identified by $^1H$ NMR experiments.

TABLE 1

Thiol Promoted Additions of $^tBuSi(Me_2)H$ to Camptothecin.

| Entry | Thiol | Temp | yield 2b | yield 3b | Recovered 1a |
|---|---|---|---|---|---|
| 1 | $^tBuSH$ | 105° C. | 22% | 10% | 57% |
| 2 | $^tC_{12}H_{25}SH$ | 105° C. | 5% | 4% | 70% |
| 3 | $(^iPr)_3SiSH$ | 105° C. | 23% | 11% | 60% |
| 4 | $(^iPr)_3SiSH$ | 160° C. | a | 22% | 20% |

<sup>a</sup>Trace product detected by TLC analysis.

Two other thiols were also studied under comparable conditions and the results are shown in Table 1, entries 2–3. Results with tert-dodecane thiol were generally inferior to tert-butane thiol. Results with triisopropylsilanethiol were similar to results using tert-butane thiol.

Solvent choices were generally limited by the solubility of camptothecin. Reactions in DMSO and tert-butanol were inferior to dioxane. Heating the reaction to 160° C. provided predominantly the 12-silyl isomer along with a greatly reduced amount of recovered camptothecin (see, for example, entry 4 in Table 1).

Thiols are known to facilitate hydrogen abstraction from silanes. While the complete mechanism of silyl radical addition to camptothecin and homocamptothecin is unclear, it is speculated that decomposition of tert-butyl peroxide to the tert-butyl peroxy radical is followed by hydrogen abstraction from the silane, the thiol and/or the solvent. Since it is present in large excess, the solvent probably reacts frequently. The resulting dioxanyl radical probably abstracts a hydrogen atom from the thiol, which in turn abstracts a hydrogen atom from the silane in a relay process. Addition of the silyl radical then occurs competitively at C7 and C12, followed by oxidative rearomatization. The generality of the reaction conditions of the present invention was shown by heating a series of silanes with triisopropylsilane thiol at the reflux point of dioxane or with tert-butyl thiol in a sealed tube at 105° C. or 160° C. The initial observations with tert-butyldimethylsilane were quite general. At the lower temperature (Table 2, entries 1–6), the 7-silylisomer 2 was isolated in 20–30% yield alongside lesser amount of the 12-silyl isomer 3 (7–19%). Most of the balance of the material was recovered camptothecin, which was reused in subsequent experiments. At the higher temperature (Table 2, entries 7–10), little or no 7-silylisomer 2 was observed and the 12-silyl isomer 3 was isolated in 22–37% yield with only 10–20% recovered camptothecin.

TABLE 2

Addition of Silyl Radicals to Campotothecin at Lower (105° C.) and Higher (160° C.) Temperatures.

| Entry | Silyl Group on Silane ($R^1R^2R^3SiH$) | Temp | 7-Silyl Isomer (C7 = Silyl, C12 = H) | | 12-Silyl Isomer (C7 = H, C12 = Silyl) | | Recovered 1 |
|---|---|---|---|---|---|---|---|
| 1  | $Et_3Si$           | 105° C. | 2c | 23% | 3c | 11% | 57% |
| 2  | $^iPrSi(Me)_2$     | 105° C. | 2d | 31% | 3d | 8%  | 61% |
| 3  | $(^iPr)_3Si$       | 105° C. | 2e | 22% | 3e | 15% | 63% |
| 4  | $PhSi(Me)_2$       | 105° C. | 2f | 23% | 3f | 7%  | 65% |
| 5  | $c$-$C_6H_{11}Si(Me)_2$ | 105° C. | 2g | 22% | 3g | 19% | 50% |
| 6  | $Et_2SiMe$         | 105° C. | 2h | 20% | 3h | 8%  | 67% |
| 7  | $Et_3Si$           | 160° C. | 2c | a   | 3c | 36% | 17% |
| 8  | $^iPrSi(Me)_2$     | 160° C. | 2d | a   | 3d | 30% | 19% |
| 9  | $c$-$C_6H_{11}Si(Me)_2$ | 160° C. | 2g | a   | 3g | 26% | 10% |
| 10 | $Et_2SiMe$         | 160° C. | 2h | a   | 3h | 26% | 10% |

[a]Trace product detected by TLC.

With the conditions for radical silylation of camptothecin generally established, the semisynthesis was applied to the synthesis of DB-67 (2a). In one study, 10-hydroxy camptothecin was first prepared from camptothecin by Pt catalyzed hydrogenation followed by $PhI(OAc)_2$ oxidation. The silylation reaction conditions set forth above were then applied to the 10-hydroxy camptothecin. The reaction gave a 14% yield of a mixture of products which contained the desired DB-67 2a based on TLC comparison with the authentic sample. However, it was difficult to isolate the desired product from the product mixture.

Figure 4:
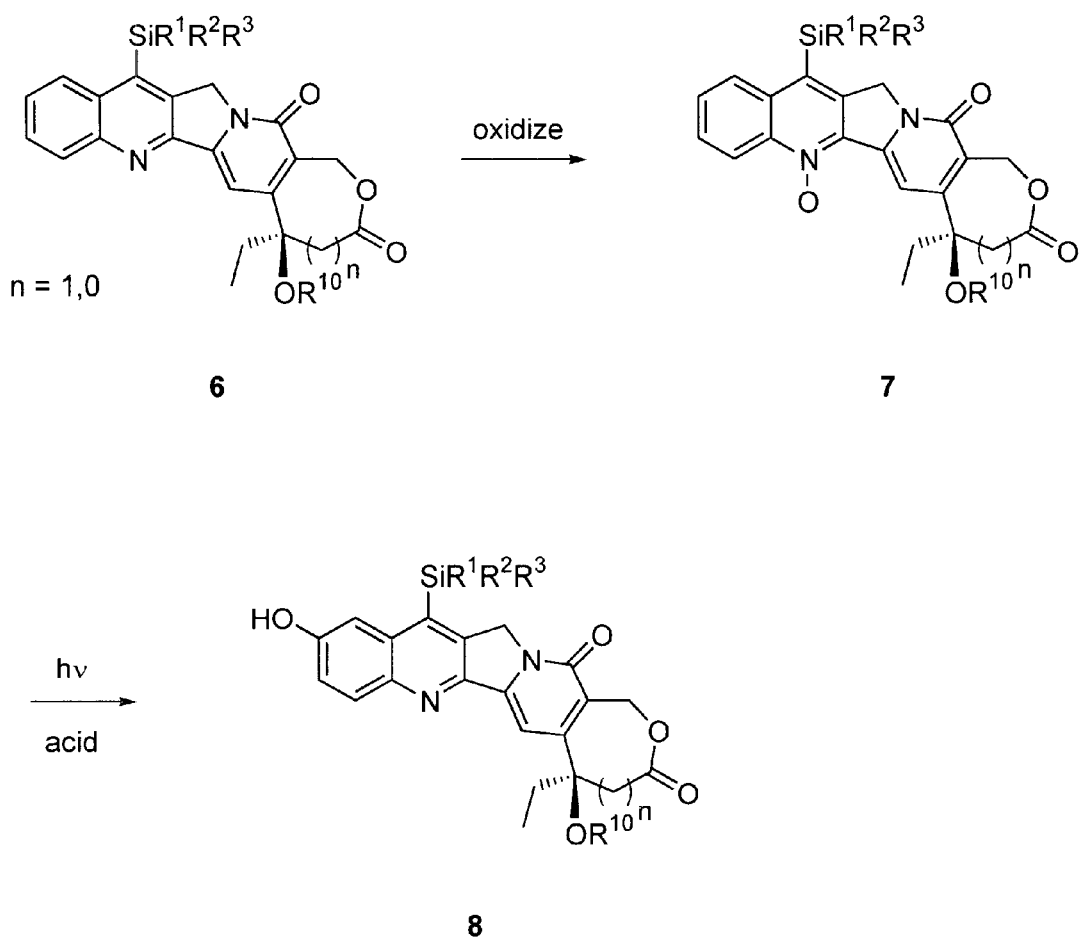
FIG. 4 illustrates a general method for converting 7-silyl camptothecins and 7-silyl homocamptothecins to 10-hydroxy-7-silylcamptothecins and 10-hydroxy-7-silylhomocamptothecins

The present invention thus also provides a two-step conversion of a 7-silyl camptothecin or a 7-silyl homocamptothecin to a 10-hydroxy-7-silyl camptothecin or a 10-hydroxy-7-silyl homocamptothecinis as illustrated in FIG. 4. The silatecan or homosilatecan derivative 6 is first oxidized to an N-oxide under conditions known to those skilled in the art for this transformation. Preferred conditions are treatment of 6 with hydrogen peroxide in the presence of a low boiling carboxylic acid, preferably acetic acid. A mixture of the resulting N-oxide 7 in an organic solvent is then irradiated with light (for example, at the edge of the ultraviolet and visible regions of the spectrum) in the presence of an organic or inorganic acid.

Figure 5:
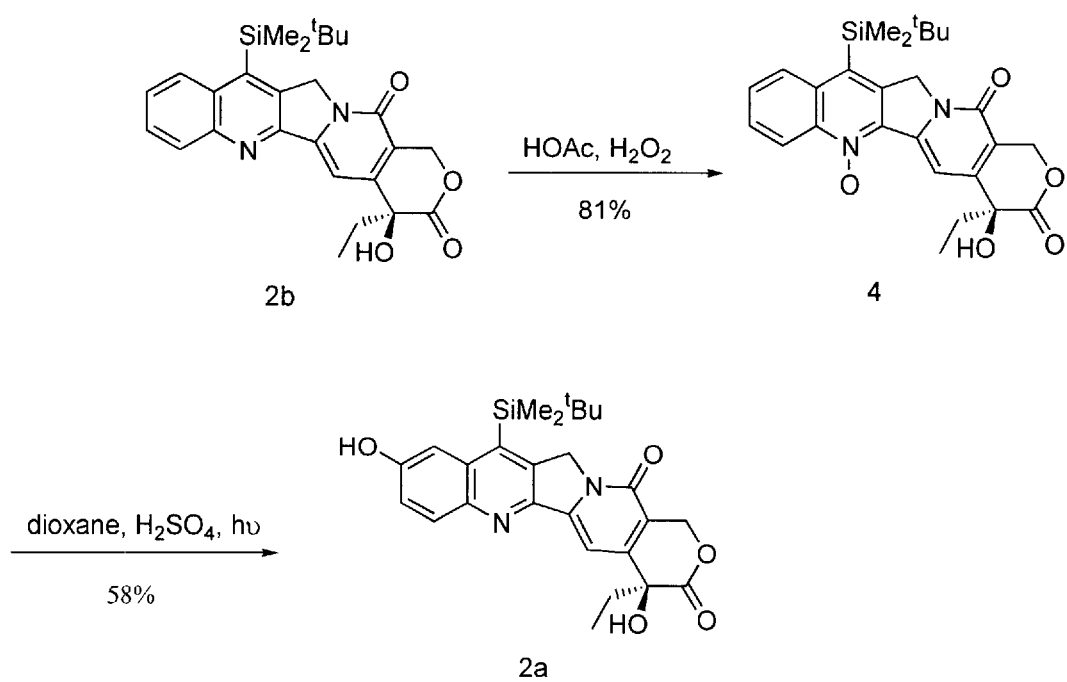
FIG. 5 illustrates conversion of 7-tert-butyldimethylsilyl camptothecin to 7-tert-butyldimethylsilyl-10-hydroxy camptothecin (DB-67).

The 10-hydroxy group of DB-67 can, therefore, also be added after the step of addition of the silyl radical to unsubstituted camptothecin. Camptothecin is readily available in large quantities. Using the above-described procedures it can now be readily converted into 7-tert-butyldimethylsilyl camptothecin 2b in about 20% yield with recovery of very substantial amounts (57%) of unreacted camptothecin. 7-tert-Butyldimethylsilyl camptothecin can be converted to DB-67 following the method illustrated in FIGS. 4 and 5. In that regard, oxidation of 2b with hydrogen peroxide in glacial acetic acid at 75° C. provided the corresponding N-oxide 4 in 81% yield. Photolysis of 4 via irradiation with a high-pressure mercury lamp in dioxane with 1 N aqueous sulfuric acid at room temperature provided DB-67 2a in 58% yield, identical to a sample of DB-67 prepared by total synthesis. This semi-synthesis occurs in about 10% overall yield for the three steps, not including the recovered camptothecin from the first step.

In general, the studies of the present invention indicate that the addition of the silyl radical to camptothecins in the methods of the present invention occurs predominately at C7 or C12 depending on temperature and can be promoted by additions of, for example, thiols. The reaction serves as a key step in short semi-syntheses of silatecans (for example, DB-67) and homosilatecans which are both significantly shorter and higher yielding than total synthesis by, for example, a cascade radical annulation approach. The increased accessibility of these silatecans and homosilatecans should facilitate their development as anti-tumor agents.

EXAMPLES

Example 1a

General Procedure for Thiol-Promoted Synthesis of 7-Silyl Camptothecins 2

To a suspension of camptothecin 1a (50 mg, 0.14 mmol) in p-dioxane (15 mL) was added the corresponding silane (0.8 mL), triisopropylsilanethiol (50 µL, 0.23 mmol) and di-tert-butyl peroxide (50 µL, 0.27 mmol)). This mixture was then refluxed under argon for 36 h, cooled and evaporated under reduced pressure. The brown residue was suspended in $CH_2Cl_2$ and applied to a silica gel column. Flash chromatography ($CH_2Cl_2$ followed by 5% acetone in $CH_2Cl_2$) yielded, in the order of elution, the 7-silyl camptothecin 2, the 12-silyl camptothecin 3, and unreacted camptothecin.

Example 1b 7-t-Butyldimethylsilyl Camptothecin (2b)

Using the general procedure 1a, 15 mg of the title compound was prepared from camptothecin (50 mg, 0.14 mmol) as yellow solid in 23% yield. The reaction also gave 12-t-butyldimethylsilylcamptothecin 3b (7 mg, 11% yield) and recovered camptothecin (30 mg, 60%). $[\alpha]_{20}^D$=+47.2 (c 2.87, $CH_2Cl_2$); IR 3357 (br), 2930, 2857, 1750 1595, 1465, 1378, 1265, 1226, 1157, 1047, 832, 728; $^1H$ NMR (300 MHz, $CDCl_3$) δ 0.714 (s, 6H), 1.00 (s, 9H), 1.05 (t, J=7.5, Hz, 3H), 1.91 (m, 2H), 3.76 (s, 1H), 5.37 (d, J=16.2 Hz, 1H), 5.33 (s, 2H), 5.77 (d, J=16.2, 1H), 7.63 (td, J=9.0, 1.5 Hz, 1H), 7.68 (s, 1H), 7.79 (td, J=7.5, 1.5 Hz, 1H), 8.23 (d, J=7.5 Hz, 1H), 8.24 (d, J=9.0 Hz, 1H); $^{13}C$ NMR ($CDCl_3$, 125 MHz) δ −0.6, 7.8, 19.2, 27.1, 31.6, 52.4, 66.3, 72.8, 97.7, 127.0, 129.4, 129.6, 130.8, 132.7, 136.0, 143.0, 146.4, 148.0, 150.2, 157.4, 173.9; HRMS m/z calcd for $C_{26}H_{30}N_2O_4Si$ 462.1975, found 462.1970.

Example 1c

7-Triethylsilyl Camptothecin (2c)

Using the general procedure 1a, 8.8 mg of the title compound was prepared from camptothecin (22 mg, 0.06 mmol) in 30% yield as yellow solid. The reaction also gave 12-triethylsilylcamptothecin 3c (3.1 mg, 11%) and recovered camptothecin (12.5 mg, 57%). $[\alpha]_{20}^D$=+38.1 (c 0.26, CH$_2$Cl$_2$); $^1$H NMR (CDCl$_3$, 300 MHz) δ 0.99 (t, J=7.9 Hz, 9H), 1.05 (t, J=7.3 Hz, 3H), 1.13 (q, J=7.9 Hz, 6H), 1.93 (m, 2H), 3.76 (s, 1H), 5.32 (d, J=16.2 Hz, 1H), 5.33 (s, 2H), 5.77 (d, J=16.2, 1H), 7.65 (td, J=7.5, 1.2 Hz, 1H), 7.68 (s, 1H), 7.80 (td, J=7.4, 0.8 Hz, 1H), 8.24 (d, J=6.6 Hz, 1H), 8.26 (d, J=7.2 Hz, 1H); HRMS m/z calcd for C$_{26}$H$_{30}$N$_2$O$_4$Si 462.1975, found 462.1985.

Example 1d

7-Isopropyldimethylsilyl Camptothecin (2d)

Using the general procedure 1a, 22 mg of the title compound was prepared in 31% yield as yellow solid from camptothecin (50 mg, 0.14 mmol). The reaction also gave 12-isopropyldimethylsilyl camptothecin 3d (6 mg, 8%) and recovered camptothecin (33.2 mg, 57%). $[\alpha]_{20}^D$=+42.1 (c 1.01, CH$_2$Cl$_2$); $^1$H NMR (CDCl$_3$, 300 MHz) δ 0.65 (s 6H), 1.00 (d, J=7.4 Hz, 3H), 1.02 (d, J=7.4 Hz, 3H), 1.05 (t, J=7.3, Hz, 3H), 1.49 (hep, 7.4 Hz, 1H), 1.91 (m, 2H), 5.32 (d, J=16.2 Hz, 1H), 5.33 (s, 2H), 5.76 (d,J=16.2, 1H), 7.65 (ddd, J=8.4, 6.7, 1.1 Hz, 1H), 7.74 (s, 1H), 7.81 (ddd, J=8.4, 7.1, 1.1 Hz, 1H), 8.23 (d, J 8.4 Hz, 1H), 8.24 (d, J=8.4 Hz, 1H); HRMS m/z calcd for C$_{25}$H$_{28}$N$_2$O$_4$Si 448.1818, found 448.1815.

Example 1e

7-Tripropylsilyl Camptothecin (2e)

Using the general procedure 1a, 16.6 mg of the title compound was prepared in 22% yield from camptothecin (50 mg, 0.14 mmol) as yellow solid. The reaction also gave 12-tripropylsilyl camptothecin 3e (11.2 mg, 15%) and recovered camptothecin (63%). $[\alpha]_{20}^D$=+39.4 (c 0.49, CH$_2$Cl$_2$); IR 3325 (br), 2956, 2927, 286 1750, 1659, 1596, 1556, 1224, 1157, 1056, 762, 728; $^1$H NMR (CDCl$_3$, 500 MHz) δ 0.98 (t, J=7.2 Hz, 9H), 1.03 (t, J=7.4, Hz, 3H), 1.15 (m, 6H), 1.35 (m, 6H), 1.91 (m, 2H) 3.75 (s, 1H), 5.32 (d, J=16.3 Hz, 1H), 5.33 (s, 2H), 5.77 (d, J=16.3, 1H), 7.66 (td, J=8.2, 1.3 Hz, 1H), 7.68 (s, 1H), 7.80 (td, J=8.0, 0.9 Hz, 1H), 8.24 (d, J=6.7 Hz, 1H), 8.27 (d, J=7.4 Hz, 1H); $^{13}$C NMR (CDCl$_3$, 125 MHz) δ 7.9, 16.7, 17.8, 18.4, 31.7, 52.0, 66.5, 72.9, 97.8, 18.2, 27.4, 128.0, 129.8, 131.2, 132.6, 135.7, 143.4, 146.6, 147.9, 150.2, 150.9, 157.6, 174.1; HRMS m/z calcd for C$_{29}$H$_{36}$N$_2$O$_4$Si 504.2444, found 504.2467.

Example 1f

7-Phenyldimethylsilyl Camptothecin (2f)

Using the general procedure 1a, 16 mg of the title compound was prepared in 23% yield from camptothecin (50 mg, 0.14 mmol) as yellow solid. The reaction also gave 12-phenyldimethylsilyl camptothecin 3f (4.6 mg, 7%) and recovered camptothecin (65%). $[\alpha]_{20}^D$=+44.9 (c 0.74, CH$_2$Cl$_2$); $^1$H NMR (300 MHz, CDCl$_3$) δ 0.90 (s, 6H), 1.03 (t, J=7.5, Hz, 3H), 1.88 (m, 2H), 4.95 (s, 2H), 5.27 (d, J=16.4 Hz, 1H), 5.71 (d, J=16.4, 1H), 7.37–7.59 (m, 6H), 7.74 (s, 1H), 7.77 (t, J=7.2, 1H), 8.14 (d, J=8.5 Hz, 1H), 8.29 (d, J=8.4 Hz, 1H); HRMS m/z calcd for C$_{28}$H$_{26}$N$_2$ O$_4$Si 482.1662, found 482.1663.

Example 1g

7—Cyclohexyldimethylsilyl Camptothecin (2g)

Using the general procedure 1a, 16.3 mg of title compound was prepared in 22% yield from camptothecin (50 mg, 0.14 mmol) as yellow solid. The reaction also gave 12-cyclohexyldimethylsilyl camptothecin 3g (19.4 mg, 19%) and recovered camptothecin (50%). $[\alpha]_{20}^D$=+27.9 (c 0.48, CH$_2$Cl$_2$); IR 3313 (br), 2919, 2845, 1749 1658, 1596, 1556, 1446, 1256, 1225, 1157, 1047, 910, 728; $^1$H NMR (500 MHz, CDCl$_3$) δ 0.64 (s, 6H), 1.05 (t, J=7.4 Hz, 3H), 1.21 (m, 6H), 1.66 (m, 5H), 1.88 (m, 2H), 3.79 (s, 2H), 5.31 (s, 2H), 5.31 (d, J=16.3 Hz, 1H), 5.76 (d, J=16.3, 1H), 7.64 (td, J=7.3, 0.9 Hz, 1H), 7.67 (s, 1H), 7.79 (t, J=7.2, 1H), 8.21 (d, J=8.0 Hz, 1H), 8.23 (d, J=7.4 Hz, 1H); $^{13}$C NMR (CDCl$_3$, 125 MHz) δ −1.4, 7.9, 26.6, 26.7, 27.5, 27.8, 31.7, 52.2, 66.5, 72.9, 97.8, 118.3, 127.3, 128.5, 129.8, 131.1, 132.4, 135.6, 143.6, 146.6, 148.0, 150.2, 150.8, 157.6, 174.1; HRMS m/z calcd for C$_{28}$H$_{32}$N$_2$O$_4$Si 488.2131, found 488.2155.

Example 1h

7-Diethylmethylsilyl Camptothecin (2h)

Using the general procedure 1a, 13.1 mg of the title compound was prepared in 20% yield from camptothecin (50 mg, 0.14 mmol) as yellow solid. The reaction also gave 12-diethylmethylsilyl camptothecin 3 h (5.2 mg, 8%) and recovered camptothecin (67%). $[\alpha]_{20}^D$=+50.0 (c 0.23, CH$_2$Cl$_2$); IR 3319 (br), 2959, 2876, 17 1658, 1595, 1557, 1225, 1157, 1047, 727; $^1$H NMR (500 MHz, CDCl$_3$) δ 0.67 (s, 3H), 0.95–1.19 (m, 13H), 1.90 (m, 2H), 3.77 (s, 1H), 5.31 (d, J=16.2 Hz, 1H), 5.33 (s,2H), 5.76 (d, J=16.2, 1H), 7.64 (td, J=8.2, 1.0 Hz, 1H), 7.68 (s, 1H), 7.79 (td, J=8.2, 0.9 Hz, 1H), 8.23 (d, J=8.7 Hz, 2H). $^{13}$C NMR (CDCl$_3$, 125 MHz) δ −2.7, 7.5, 7.7, 7.9, 31.7 52.1, 66.5, 72.9, 97.8, 118.3, 127.4, 128.1, 129.8, 131.1, 132.4, 135.7, 143.0, 146.6, 148.0, 150.2, 150.9, 157.6, 174.1. HRMS m/z calcd for C$_{25}$, H$_{28}$N$_2$O$_4$Si 448.1818, found 448.1815.

Example 1i (±) 7-t-Butyldimethylsilyl Homocamptothecin

Using the general procedure 1a, the title compound was prepared in 10% yield in addition to 62% of recovered (±) hCPT: $^1$H NMR (300 MHz, CDCl$_3$) δ 0.73 (s, 6H), 0.99 (t, 7.5 Hz, 3H), 1.03 (s, 9H), 2.05 (m, 2H), 3.21 (d, 13.6 Hz, 1H), 3.48 (d, 13.6 Hz, 1H), 5.23 (d, 19 Hz, 1H), 5.36 (d, 15.3 Hz, 1H), 5.39 (d, 19 Hz, 1H), 5.71 (d, 15.3 Hz, 1H), 7.46 (s, 1H), 7.55 (m, 1H), 7.65 (m, 1H), 7.99 (d, 8.6 Hz, 1H), 8.18 (d, 8.0 Hz, 1H).

Example 1j

Silylation of CPT-N-oxide

Using the general procedure 1a, camptothecin-N-oxide (30 mg, 0.08 mmol) yielded 7-t-butyldimethylsilylcamptothecin (8 mg, 20% yield) and camptothecin (17 mg, 60%). 12-t-butyldimethylsilylcamptothecin was observed in TLC and was isolated as a mixture with other byproducts.

Example 2a

General Procedure for Thiol-Promoted Synthesis of 12-Silyl Camptothecins

To a suspension of camptothecin 1a (20 mg, 0.057 mmol) in dioxane (2 mL) in a pressure tube was added the corresponding silane (0.5 mL) followed by 20 μL of di-tert-butyl peroxide (20 μL, 0.09 mmol) and 20 μL of triisopropylsilanethiol (20 μL, 0.11 mmol). The pressure tube was then sealed and heated to 160° C. for 16 h. After evaporation of the volatile components, the residue was purified by flash chromatography (5% acetone in dichloromethane) on silica gel column to give the 12-silyl camptothecin 3 and recovered camptothecin.

Example 2b

12-t-Butyldimethylsilyl Camptothecin (3b)

Using the general procedure 2a, 5.8 mg of the title compound was prepared from camptothecin (20 mg, 0.057 mmol) in 22% yield as pale yellow solid, in addition to recovered camptothecin (20%). $[\alpha]_{20}^D=+75.0$ (c 0.04 $CH_2Cl_2$); IR 3380 (br), 2927, 2854, 1747, 1658, 1602, 1557, 1487, 1401, 1247, 1223, 1157, 1046, 840, 769, 732; $^1H$ NMR (500 MHz, $CDCl_3$) δ 0.56 (s, 6H), 0.98 (s, 9H), 1.06 (t, J=7.4 Hz, 3H), 1.94 (m, 2H), 3.76 (s, 1H), 5.31 (s, 2H), 5.32 (d, J=16.1 Hz, 1H). 5.77 (d, J=16.1 Hz, 1H), 7.54 (s, 1H), 7.64 (t, J=7.4 Hz, 1H), 7.93 (d, J=7.4 Hz, 1H), 8.00 (d, J=7.4 Hz, 1H), 8.37 (s, 1H); $^{13}C$ NMR (125 MHz, $CDCl_3$) δ −3.3, 7.8, 17.7, 27.7, 31.5, 50.3, 66.5, 72.8, 97.7, 118.3, 127.4, 127.9, 129.3, 131.3, 138.6, 141.1, 147.1, 150.3, 151.1, 153.3, 157.8, 174.1; HRMS m/z calcd for $C_{26}H_{30}N_2O_4Si$ 462.1975, found 462.1972.

Example 2c

12-Triethylsilyl Camptothecin (3c)

Using the general procedure 2a, 9.8 mg of the title compound was prepared from camptothecin (20 mg, 0.057 mmol) in 37% yield as pale yellow solid in addition to recovered camptothecin (19%). $[\alpha]_{20}^D=+16.1$ (c 0.33, $CH_2Cl_2$); IR 2926, 2874, 1744, 1659, 1603, 1557, 1463, 1224, 1157, 908, 733; $^1H$ NMR (500 MHz, $CDCl_3$) δ 0.97 (t, J=7.5 Hz, 9H), 1.08 (m, 6H), 1.06 (t, J=7.4 Hz, 3H), 1.93 (m, 2H), 3.79 (s, 1H), 5.31 (s, 2H), 5.33 (d, J=16.2 Hz, 1H). 5.78 (d, J=16.2 Hz, 1H), 7.54 (s, 1H), 7.63 (dd, J=7.9, 6.9 Hz, 1H), 7.92 (d, J=7.9 Hz, 1H), 7.96 (d, J=6.9 Hz, 1H), 8.37 (s, 1H); $^{13}C$ NMR (125 MHz, $CDCl_3$) δ 4.4, 7.8, 29.8, 31.6, 50.2, 66.5, 72.8, 97.5, 118.3, 127.5, 127.8, 128.0, 129.1, 131.4, 138.3, 140.2, 147.2, 150.3, 151.2, 153.3, 157.8, 174.0; HRMS m/z calcd for $C_{26}H_{30}N_2O_4Si$ 462.1975, found 462.1973.

Example 2d

12-Isopropyldimethylsilyl Camptothecin (3d)

Using the general procedure 2a, 7.7 mg of the title compound was prepared from camptothecin (20 mg, 0.057 mmol) in 30% yield as pale yellow solid in addition to recovered camptothecin (19%). $[\alpha]_{20}^D=+62.5$ (c 0.04, $CH_2Cl_2$); IR 3346 (br), 2945, 2863, 1747, 1657, 1602, 1558, 1486, 1401, 1245, 1223, 1157, 1046, 1002, 909, 841, 767, 732; $^1H$ NMR (500 MHz, $CDCl_3$) δ 0.48 (s, 6H), 0.98 (d, J=7.4 Hz, 3H), 1.0 (d, J=7.4 Hz, 3H), 1.06 (t, J=7.4 Hz, 3H), 1.49 (m, 1H), 1.92 (m, 2H), 3.78 (s, 1H), 5.30 (s, 2H), 5.32 (d, J=16.2 Hz, 1H). 5.77 (d, J=16.2 Hz, 1H), 7.52 (s, 1H), 7.62 (dd, J =7.9, 6.8 Hz, 1H), 7.92 (d, J=7.9 Hz, 1H), 7.97 (d, J=6.8 Hz, 1H), 8.37 (s, 1H); $^{13}C$ NMR (125 MHz, $CDCl_3$) δ −3.8, −3.6, 7.9, 14.0, 18.1, 31.5, 50.2, 66.5, 72.8, 96.2, 118.3, 127.5, 127.8, 128.0, 129.2, 131.4, 137.8, 141.5, 147.1, 150.4, 151.1, 153.1, 157.8, 174.0; HRMS m/z calcd for $C_{25}H_{28}N_2O_4Si$ 448.1818, found 448.1815.

Example 2e

12-Tripropylsilyl Camptothecin (3e)

This compound was isolated from the reaction described in Example 1e. $[\alpha]_{20}^D=+13.2$ (c 0.79 $CH_2Cl_2$); IR 3348, 2961, 2926, 2873, 1755, 1661, 1603, 1491, 1462, 1403, 1374, 1333, 1228, 1163, 1064, 1005, 841; $^1H$ NMR (300 MHz, $CDCl_3$) δ 0.95 (t, J=7.1 Hz, 3H), 1.05–1.12 (m, 9H), 1.38 (m, 6H), 1.93 (m, 2H), 3.75 (s, 1H), 5.31 (s, 2H), 5.33 (d, J=16.3 Hz, 1H). 5.78 (d, J=16.3 Hz, 1H), 7.56 (s, 1H), 7.62 (dd, J=8.1, 6.7 Hz 1H), 7.91 (dd, J=8.1, 1.0 Hz, 1H), 7.95 (dd, J=6.7, 1.3 Hz, 1H), 8.36 (s, 1H); $^{13}C$ NMR (125 MHz, $CDCl_3$) δ 7.8, 16.5, 17.9, 18.8, 31.6, 50.3, 66.5, 72.8, 97.6, 118.3, 127.5, 127.8, 128.0, 129.1, 131.3, 137.9, 141.1, 147.1, 150.3, 151.2, 153.3, 157.85, 174.2; HRMS m/z calcd for $C_{29}H_{36}N_2O_4Si$ 504.2444, found 504.2450.

Example 2f

12-Dimethylphenylsilyl Camptothecin (3f)

This compound was isolated from the reaction described in Example 1f. $[\alpha]_{20}^D=+11.3$ (c 0.53 $CH_2Cl_2$); IR 3365, 2973, 2961, 1750, 1666, 1604, 1559, 1492, 1251, 1234, 1155, 1110, 1049, 830; $^1H$ NMR (300 MHz, $CDCl_3$) δ 0.83 (s, 6H), 1.09 (t, J=7.4 Hz, 3H), 1.94 (m, 2H), 3.80 (s, 1H), 5.24 (s, 2H), 5.32 (d, J=16.3 Hz, 1H). 5.76 (d, J=16.3 Hz, 1H), 7.37 (m, 3H), 7.53 (s, 1H), 7.59 (dd, J=7.5, 7.4 Hz, 1H), 7.78 (m, 2H), 7.89 (m, 2H), 8.30 (s, 1H); $^{13}C$ NMR (125 MHz, $CDCl_3$) δ −1.3, 7.9, 31.6, 33.9, 50.2, 66.5, 72.8, 97.7, 118.4, 127.6, 127.8, 128.1, 129.0, 129.6, 131.3, 134.5, 138.0, 139.1, 141.0, 146.9, 150.3, 151.2, 152.9, 157.8, 174.1; HRMS m/z calcd for $C_{28}H_{26}N_2O_4Si$ 482.1662, found 482.1684.

Example 2g

12—Cyclohexyldimethylsilyl Camptothecin (3g)

Using the general procedure 2a, 7.3 mg of the title compound was prepared from camptothecin (20 mg, 0.057 mmol) in 26% yield as pale yellow solid in addition to recovered camptothecin (10%). $[\alpha]_2^D=+33.3$ (c 0.09, $CH_2Cl_2$); IR 3363 (br), 2918, 2845, 1745, 1657, 1602, 1558, 1486, 1401, 1245, 1223, 1157, 1046, 909, 837, 768, 732; $^1H$ NMR (500 MHz, $CDCl_3$) δ 0.46 (s, 6H), 1.07 (t, J=7.3 Hz, 3H), 1.18 (br, 6H), 1.67 (br, 5H), 1.94 (m, 2H), 3.76 (s, 1H), 5.30 (s, 2H), 5.32 (d, J=16.2 Hz, 1H). 5.77 (d, J=16.2 Hz, 1H), 7.56 (s, 1H), 7.62 (t, J=7.4 Hz, 1H), 7.91 (d, J=7.4 Hz, 1H), 7.95 (d, J=7.4 Hz, 1H), 8.36 (s, 1H); $^{13}C$ NMR (125 MHz, $CDCl_3$) δ −3.4, 7.8, 26 27.1, 28.1, 28.4, 31.5, 50.3, 66.5, 72.8, 97.6, 118.3, 127.5, 127.8, 128.0, 129.1, 131.3, 137.7, 141.6, 147.1, 150.3, 151.1, 153.1, 157.8, 174.2; HRMS m/z calcd for $C_{28}H_{32}N_2O_4Si$ 488.2131 found 488.2133.

Example 2h

12-Diethylmethylsilyl Camptothecin (3h)

Using the general procedure 2a, 7 mg of the title compound was prepared from camptothecin (20 mg, 0.057 mmol) in 26% yield as pale yellow solid in addition to recovered camptothecin (10%). $[\alpha]_{20}^D=+50.0$ (c 0.05, $CH_2Cl_2$); IR 3389 (br), 2953, 2874, 1746, 1659, 1602, 1555, 1486, 1402, 1223, 1157, 1046, 1004, 908, 838,787,732; $^1H$ NMR (500 MHz, $CDCl_3$) δ 0.48 (s, 3H), 0.9–1.1 (m, 13H), 1.96 (m, 2H), 3.79 (s, 1H), 5.31 (s, 2H), 5.33 (d, J=16.2 Hz, 1H). 5.78 (d, J=16.2 Hz, 1H), 7.53 (s, 1H), 7.63 (t, J=7.4 Hz, 1H), 7.92 (d, J=7.4 Hz, 1H), 7.97 (d, J=7.4 Hz, 1H), 8.37 (s, 1H); $^{13}C$ NMR (125 MHz, $CDCl_3$) δ −4.5, 6.5, 7.9, 31.6, 50.2, 66.5, 72.8, 97.4, 118.3, 127.5, 127.8, 128.0, 129.2, 131.4, 137.8, 141.0, 147.2, 150.4, 151.1, 153.2, 157.8, 174.0; HRMS m/z calcd for $C_{25}H_{28}N_2O_4Si$ 448.1818, found 448.1824.

Example 3

7-tert-Butyldimethylsilyl Camptothecin N-oxide (4)

To the solution of 7-t-butyldimethylsilyl camptothecin (50 mg, 0.11 mmol) in glacial acetic acid (10 mL) was added 30% $H_2O_2$ (0.8 mL, 7 mmol). This solution was then gently heated at 75° C. for 3 h, then it was evaporated to dryness under reduced pressure. The orange residue was purified by flash chromatography (15% acetone in $CH_2Cl_2$) on silica gel to give 40.3 mg of 7-tert-butyldimethylsilyl-camptothecin-N-oxide as pale orange powder in 81% yield. $[\alpha]_{20}^D$=+10.0 (c 0.46, $CH_2Cl_2$); IR 3342 (br), 2933,2884,2857, 1750, 1654, 1596, 1557, 1499, 1464, 1258, 1224, 1160, 1090, 821; $^1$H NMR (CDCl$_3$, 300 MHz) δ 0.71 (s, 6H), 1.00 (s, 9H), 1.06 (t, J=7.2, Hz, 3H), 1.88 (m, 2H), 5.28 (d, J=16.8 Hz, 1H), 5.32 (s, 2H), 5.72 (d, J=16.8, 1H), 7.69 (t, J=7.7 Hz, 1H), 7.79 (t, J=7.8 Hz, 1H), 8.26 (d, J=8.4 Hz, 1H), 8.40 (s, 1H), 8.84 (d, J=8.4 Hz, 1H); $^{13}$C NMR (CDCl$_3$ 125 MHz) δ −0.2, 0.0, 8.2, 19.8, 27.5, 32.1, 53.4, 66.4, 73.0, 103.1, 119.7, 129.0, 130.2, 130.4, 131.3, 134.9, 136.2, 138.3, 141.0, 141.4, 150.8, 157.2, 173.8, 207.5; HRMS m/z calcd for $C_{26}H_{30}N_2O_5Si$ 478.1924, found 478.1902.

Example 4

10-Hydroxy-7-fert-butyldimethylsilyl Camptothecin (2a) by Photolysis

A 100 mL pyrex round bottom flask was charged with 7-tert-butyldimethylsilyl-camptothecin-N-oxide (36 mg, 0.075 mmol) and degassed dioxane (30 mL). To this solution was then added 1 N aqueous $H_2SO_4$ (80 µL, 0.08 mmol). The resulting solution was photolyzed by high pressure Hg lamp for 80 min. The reaction mixture was then evaporated to dryness, and the residue was purified by flash chromatography (20% acetone in $CH_2Cl_2$) on silica gel to give 9.8 mg of combined mixture of 7-tert-butyldimethylsilyl-camptothecin and unreacted 7-tert-butyldimethylsilyl-camptothecin-N-oxide, and 20.7 mg of the title compound as yellow powder in 58% yield. $[\alpha]_{20}^D$=+22.8 (c 1.89, $CH_2Cl_2$/MeOH 4:1); $^1$H NMR (CDCl$_3$, 300 MHz) δ 0.68 (s, 6H), 0.96 (s, 9H), 1.03 (t, J=7.2, Hz, 3H), 1.88 (m, 2H), 3.77 (br, 1H), 5.31 (d, J=16.2 Hz, 1H), 5.31 (s, 2H), 5.75 (d, J=16.2, 1H), 7.47 (dd, J=9.0, 1.8 Hz, 1H), 7.61 (d, J=1.8 Hz, 1H), 7.78 (s, 1H), 8.22 (d, J=9.0 Hz, 1H); HRMS (—CO$_2$) m/z calcd for $C_{25}H_{30}N_2O_3Si$ 434.2026, found 434.2009.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of synthesizing a compound having the formula

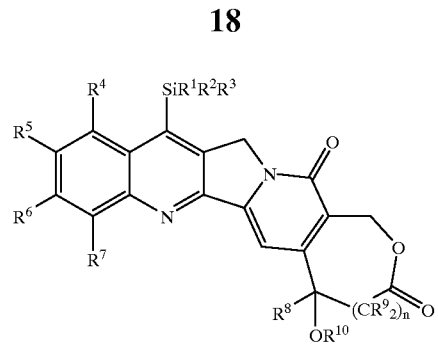

in racemic form, enantiomerically enriched form or enantiomerically pure form the method including the steps of:
reacting a compound having the formula

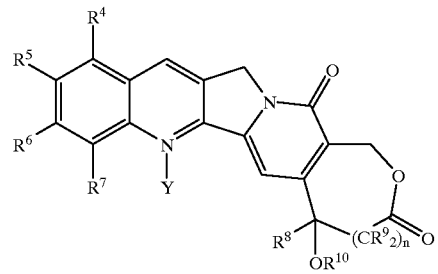

with a silyl radical precursor under conditions to generate a silyl radical. $SiR^1R^2R^3$ wherein $R^1$, $R^2$ and $R^3$ are independently a $C_{1-10}$ alkyl group, a $C_{2-10}$ alkenyl group, a $C_{2-10}$ alkynyl group, an aryl group, —(CH$_2$)$_m$R$^{11}$ group or $SiR^{12}R^{13}R^{14}$, wherein m is an integer within the range of 1 through 10, $R^{11}$ is a hydroxy group, an alkoxy group, an amino group, an alkylamino group, a dialkylamino group, F, Cl, a cyano group, —SR$^c$ or a nitro group, and wherein $R^{12}$, $R^{13}$ and $R^{14}$ are independently the same or different an alkyl group or an aryl group;

wherein $R^4$ and $R^5$ are independently the same or different and are hydrogen, —C(O)R$^f$ wherein R$^f$ is an alkyl group, an alkoxy group, an amino group or a hydroxy group, an alkyl group, an alkenyl group, an alkynyl group, an alkoxy group, an aryloxy group, an acyloxy group, —OC(O)OR$^d$, wherein R$^d$ is an alkyl group, —OC(O)NR$^a$R$^b$ wherein R$^a$ and R$^b$ are independently the same or different, H, —C(O)R$^f$, an alkyl group or an aryl group, F, Cl, a hydroxy group, a nitro group, a cyano group, an azido group, a formyl group, a hydrazino group, an amino group, —SR$^c$, wherein R$^c$ is hydrogen, —C(O)R$^f$, an alkyl group or an aryl group; or $R^4$ and $R^5$ together form a chain of three or four members selected from the group of CH, CH$_2$, O, S, NH, or NR$^{15}$, wherein $R^{15}$ is an $C_1$–$C_6$ alkyl group;

$R^6$ is H, F, Cl, a nitro group, an amino group, a hydroxy group, or a cyano group; or $R^5$ and $R^6$ together form a chain of three or four members selected from the group of CH, CH$_2$, O, S, NH, or NR$^{15}$;

$R^7$ is H, F, an amino group, a $C_{1-3}$ alkyl group, a $C_{2-3}$ alkenyl group, a $C_{2-3}$ alkynyl group, a trialkylsilyl group or a $C_{1-3}$ alkoxy group;

$R^8$ is a $C_{1-10}$ alkyl group, an alkenyl group, an alkynyl group, or a benzyl group;

$R^9$ is H, F or —CH$_3$;

n is 0 or 1;

$R^{10}$ is —C(O)$R^f$ or H; and

Y is absent or is O.

2. The method of claim 1 wherein the silyl radical precursor has the formula XSi$R^1R^2R^3$ wherein X is H, Si$R^{17}R^{18}R^{19}$, Ge$R^{17}R^{18}R^{19}$, Sn$R^{17}R^{18}R^{19}$, —B(O$R^d$)$_2$ or —C(O)$R^i$, wherein $R^{17}$, $R^{18}$ and $R^{19}$ are independently an aryl group or an alkyl group and wherein $R^i$ is an alkyl group or an aryl group.

3. The method of claim 1 wherein $R^8$ is an ethyl group, an allyl group, a benzyl group or a propargyl group.

4. The method of claim 1 wherein $R^8$ is an ethyl group.

5. The method of claim 1 wherein $R^9$ is H.

6. The method of claim 1 wherein $R^{10}$ is H or C(O)CH$_3$.

7. The method of claim 2 wherein X is H.

8. The method of claim 1 wherein $R^4$, $R^5$, $R^6$, and $R^7$ are H.

9. The method of claim 2 wherein $R^1$ and $R^2$ are methyl groups, $R^3$ is a tert-butyl group or a methyl group, $R^4$ is H, $R^6$ is H and $R^7$ is H.

10. The method of claim 9 wherein $R^5$ is H, NH$_2$ or OH.

11. The method of claim 2 wherein X is H and the silyl radical is generated by reacting the silyl radical precursor with a radical generator.

12. The method of claim 10 wherein the X is H or Si$R^{17}R^{18}R^{19}$ and the radical generator is a peroxide.

13. The method of claim 12 wherein X is H and the silyl radical is generated in the presence of a thiol.

14. The method of claim 13 wherein $R^4$, $R^5$, $R^6$, $R^7$ and $R^{10}$ are H and $R^8$ is an ethyl group.

15. The method of claim 14 wherein n is 0.

16. The method of claim 15 further including the step of converting $R^5$ to OH.

17. The method of claim 16 wherein the step of converting $R^5$ to OH includes the step of oxidation to provide an N-oxide, followed by the step of photolysis.

18. The method of claim 17 wherein the step of oxidation includes the addition of hydrogen peroxide in a carboxylic acid.

19. The method of claim 18 wherein the step of photolysis occurs in dioxane with an acid.

20. The method of claim 13 wherein the reaction temperature is in the range of approximately 60 to approximately 130° C.

21. A method of synthesizing 7-silyl camptothecins and 7-silyl homocamptothecins including the step of mixing a camptothecin or a homocamptothecin having hydrogen at the C7 position with a silyl radical generator and a silyl radical precursor under conditions to generate a silyl radical. Si$R^1R^2R^3$ wherein $R^1$, $R^2$ and $R^3$ are independently a C$_{1-10}$ alkyl group, a C$_{2-10}$ alkenyl group, a C$_{2-10}$ alkynyl group, an aryl group, —(CH$_2$)$_m R^{11}$ or Si$R^{12}R^{13}R^{14}$, wherein m is an integer within the range of 1 through 10 and $R^{11}$ is a hydroxy group, an alkoxy group, an amino group, an alkylamino group, a dialkylamino group, F, Cl, a cyano group, —S$R^c$ or a nitro group, and wherein $R^{12}$, $R^{13}$ and $R^{14}$ are independently the same or different an alkyl group or an aryl group.

22. The method of claim 21 wherein the silyl radical precursor has the formula XSi$R^1R^2R^3$ wherein X is H, Si$R^{17}R^{18}R^{19}$, Ge$R^{17}R^{18}R^{19}$, Sn$R^{17}R^{18}R^{19}$, —B(O$R^d$)$_2$ or —C(O)$R^i$, wherein $R^{17}$, $R^{18}$ and $R^{19}$ are independently an aryl group or an alkyl group and wherein $R^i$ is an alkyl group or an aryl group.

23. The method of claim 22 wherein X is H or Si$R^{17}R^{18}R^{19}$, the generator is a peroxide, and the silyl radical is generated in the presence of a thiol.

24. The method of claim 23 wherein the camptothecin is unsubstituted camptothecin, $R^1$ and $R^2$ are methyl groups, and $R^3$ is a tert-butyl group.

25. The method of claim 24 further including the step of replacing the hydrogen at the C10 position of the resultant 7-tert-butyldimethylsilyl camptothecin with OH.

26. The method of claim 25 wherein the step of replacing the hydrogen at the C10 position with OH includes the step of oxidation to provide an N-oxide, followed by the step of photolysis.

27. The method of claim 26 wherein the step of oxidation includes the addition of hydrogen peroxide in a carboxylic acid.

28. The method of claim 27 wherein the step of photolysis occurs in dioxane with an acid.

29. The method of claim 23 wherein the reaction temperature is in the range of approximately 60 to approximately 130° C.

30. The method of claim 22 wherein $R^1$, $R^2$ and $R^3$ are independently a C$_{1-10}$ alkyl group or an aryl group.

31. A method of synthesizing 10-hydroxy-7-silylcamptothecins or a 10-hydroxy-7-silyl homocamptothecins including the step of converting hydrogen at the C10 position of a 7-silyl camptothecin or a 7-silyl homocamptothecin to —OH by oxidation of the 7-silyl camptothecin or the 7-silyl homocamptothecin to provide an N-oxide, followed by photolysis.

32. The method of claim 31 wherein the step of oxidation includes the addition of hydrogen peroxide in a carboxylic acid.

33. The method of claim 32 wherein the carboxylic acid is acetic acid.

34. The method of claim 33 wherein the step of photolysis occurs in dioxane with an acid.

35. The method of claim 34 wherein the acid is sulfuric acid.

36. The method of claim 31 wherein the wavelength of irradiated light during photolysis is in the range of approximately 250–600 nm.

37. The method of claim 36 wherein the wavelength of irradiated light during photolysis is in the range of approximately 275–450 nm.

38. The method of claim 31 wherein the compound converted is 7-silyl camptothecin.

39. A compound having the formula:

wherein $R^1$, $R^2$ and $R^3$ are independently a C$_{1-10}$ alkyl group, a C$_{2-10}$ alkenyl group, a C$_{2-10}$ alkynyl group, an aryl group, —(CH$_2$)$_m R^{11}$ group or Si$R^{12}R^{13}R^{14}$, wherein m is an integer within the range of 1 through 10, $R^{11}$ is a hydroxy group, an alkoxy group, an amino group, an alkylamino group, a dialkylamino group, F, Cl, a cyano group, —S$R^c$ or a nitro group, and wherein $R^{12}$, $R^{13}$ and $R^{14}$ are independently the same or different an alkyl group or an aryl group;

wherein $R^4$ and $R^5$ are independently the same or different and are hydrogen, —C(O)$R^f$ wherein $R^f$ is an alkyl group, an alkoxy group, an amino group or a hydroxy group, an alkyl group, an alkenyl group, an alkynyl group, an alkoxy group, an aryloxy group, an acyloxy group, —OC(O)O$R^d$, wherein $R^d$ is an alkyl group, —OC(O)N$R^a R^b$ wherein $R^a$ and $R^b$ are independently the same or different, H, —C(O)$R^f$, an alkyl group or an aryl group, F, Cl, a hydroxy group, a nitro group, a cyano group, an azido group, a formyl group, a hydrazino group, an amino group, —S$R^c$, wherein $R^c$ is hydrogen, —C(O)$R^f$, an alkyl group or an aryl group; or $R^4$ and $R^5$ together form a chain of three or four members selected from the group of CH, $CH_2$, O, S, NH, or $NR^{15}$, wherein $R^{15}$ is an $C_1$–$C_6$ alkyl group;

$R^6$ is H, F, Cl, a nitro group, an amino group, a hydroxy group, or a cyano group; or $R^5$ and $R^6$ together form a chain of three or four members selected from the group of CH, $CH_2$, O, S, NH, or $NR^{15}$;

$R^7$ is H, F, an amino group, a $C_{1-3}$ alkyl group, a $C_{2-3}$ alkenyl group, a $C_{2-3}$ alkynyl group, a trialkylsilyl group or a $C_{1-3}$ alkoxy group;

$R^8$ is a $C_{1-10}$ alkyl group, an alkenyl group, an alkynyl group, or a benzyl group;

$R^9$ is H, F or —$CH_3$; n is 0 or 1; and $R^{10}$ is —C(O)$R^f$ or H.

\* \* \* \* \*